US008419644B2

(12) United States Patent
Eerden

(10) Patent No.: US 8,419,644 B2
(45) Date of Patent: Apr. 16, 2013

(54) CORDLESS CHARGER FOR A WEARABLE PATIENT MONITOR

(75) Inventor: Jacco C. Eerden, Kirkland, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1117 days.

(21) Appl. No.: 12/302,350

(22) PCT Filed: May 1, 2007

(86) PCT No.: PCT/US2007/067850
§ 371 (c)(1),
(2), (4) Date: Nov. 25, 2008

(87) PCT Pub. No.: WO2007/140069
PCT Pub. Date: Dec. 6, 2007

(65) Prior Publication Data
US 2009/0163820 A1    Jun. 25, 2009

Related U.S. Application Data

(60) Provisional application No. 60/803,164, filed on May 25, 2006.

(51) Int. Cl.
*A61B 5/02* (2006.01)
(52) U.S. Cl.
USPC ........... 600/481; 600/300; 600/301; 600/372; 600/384; 320/103; 320/112; 320/113; 320/114; 320/137; 320/161; 340/539.12; 455/73
(58) Field of Classification Search .................. 600/300, 600/301, 481; 128/903–905, 920; 320/107–115, 320/125
See application file for complete search history.

(56) References Cited

U.S. PATENT DOCUMENTS

| 4,288,733 | A | * | 9/1981  | Bilanceri et al. ............. 320/113 |
| 5,228,449 | A |   | 7/1993  | Christ et al. |
| 5,396,162 | A | * | 3/1995  | Brilmyer ..................... 320/114 |
| 5,557,188 | A | * | 9/1996  | Piercey ......................... 320/134 |
| 5,558,638 | A | * | 9/1996  | Evers et al. ..................... 604/66 |
| 5,565,756 | A | * | 10/1996 | Urbish et al. ................. 320/103 |
| 5,565,759 | A | * | 10/1996 | Dunstan ........................ 320/135 |
| 5,568,038 | A |   | 10/1996 | Tatsumi |

(Continued)

FOREIGN PATENT DOCUMENTS

| EP | 0940903 A2 | 9/1999 |
| WO | 9959465 A1 | 11/1999 |
| WO | 02067122 A1 | 8/2002 |

*Primary Examiner* — Bill Thomson
*Assistant Examiner* — Marie Archer

(57) ABSTRACT

The present application discloses a cordless charger for a wearable patient monitor. When a patient (10) is diagnosed with a heart condition, or suspected heart condition, they are prescribed a patient monitoring system. The system includes monitors (12) that the patient (10) wears to collect the data of interest. Each day, the patient swaps the monitor (12) he or she is wearing with a fully charged monitor (12) from a cordless charger (14). In this manner, a fresh monitor (12) is always available for monitoring the patient (10). The cordless charger (14) includes a battery (50) that powers the processes of the charger and recharges batteries (34) of the monitors (12). Data from the monitors can be either offloaded to the charger memory (70), or transmitted to a remote database (32) via the patient's Bluetooth enabled cellular phone (30) or other like device.

21 Claims, 5 Drawing Sheets

U.S. PATENT DOCUMENTS

| | | | |
|---|---|---|---|
| 6,018,227 A * | 1/2000 | Kumar et al. | 320/106 |
| 6,184,655 B1 * | 2/2001 | Malackowski | 320/116 |
| 6,238,338 B1 * | 5/2001 | DeLuca et al. | 600/300 |
| 6,624,616 B1 * | 9/2003 | Frerking et al. | 320/162 |
| 6,737,830 B2 | 5/2004 | Bean et al. | |
| 7,201,719 B2 * | 4/2007 | Feliss et al. | 600/300 |
| 7,554,285 B2 * | 6/2009 | Simoes et al. | 320/103 |
| 7,570,994 B2 * | 8/2009 | Tamura et al. | 607/5 |
| 2004/0147293 A1 * | 7/2004 | Park | 455/573 |
| 2005/0288559 A1 | 12/2005 | Feliss et al. | |

* cited by examiner

CORDLESS CHARGER FOR A WEARABLE PATIENT MONITOR

CROSS REFERENCE TO RELATED APPLICATIONS

This application claims the benefit of U.S. provisional application Ser. No. 60/803,164 filed May 25, 2006, which is incorporated herein by reference.

The present application relates to use in the diagnostic arts, It finds particular application in wireless heart monitors that are intended to be used by a patient for a limited period of time, e.g. a month. However, it also finds application in wireless monitors for different purposes and for different usage durations.

People can experience cardiac arrhythmias or syncopal events at unpredictable intervals. These events can be difficult to catch and monitor at a physician's office due to their infrequent nature.

Also, there is a trend toward releasing hospital patients earlier after surgery or a medical event, such as a heart attack. It would be advantageous to monitor the cardiac function for a limited duration after release.

Typically, patients in need of short term monitoring are equipped with monitors designed for long term use. The monitors may require frequent, e.g. daily, battery replacement or charging. Others have larger batteries to extend the time between charging or replacement. Because batteries are heavy, devices with larger batteries are less comfortable to wear.

While rechargeable batteries are convenient, they require a battery charger. Changing the monitor often involves changing a patch or other body mounting, which is adhered to the patient's chest. Hence, the monitors are typically changed and recharged in the bathroom, where the charger is plugged in. This, disadvantageously, introduces another device with a power cable and plug into the bathroom. There is often little space to put these devices and limited outlets, both of which may already be allocated to power toothbrushes, hair dryers, curling irons, shavers, or the like. In addition to limited space and limited outlets, sometimes outlets are not available, or have different power outputs, making them useless without a converter. This may happen, for example, when traveling to jurisdictions where outlets have higher or lower wall plug voltage standards.

The present application provides a new and improved patient monitoring system which overcomes the above-referenced problems and others.

In accordance with one aspect, a patient monitoring system is disclosed. At least one wearable patient monitor monitors an aspect of a patient's physiology. The monitor has a rechargeable power source. A cordless charger charges the power source. A data transfer system transfers data from the monitor to a processor or memory at a remote location.

In accordance with another aspect, a method of patient monitoring is disclosed. At least one aspect of a patient's physiology is monitored with a first wearable patient monitor with its own rechargeable power source. Data is transferred from the first monitor to a processor or database. The first monitor is exchanged with a second monitor so that the first monitor can recharge in a cordless charging unit.

In accordance with another aspect, a patient monitoring system is disclosed. A first means for monitoring monitors at least one aspect of a patient's physiology. The means for monitoring includes a data storage means. A data transfer means transfers data from the monitoring means to a data storage means. A second means for monitoring also monitors the aspect of the patient's physiology, and a means for cordlessly recharging recharges the monitoring means.

One advantage resides in increased convenience for the patient.

Another advantage resides in the safety of low voltages.

Another advantage resides in simplified portability of the charger.

Another advantage resides in ease of travel among jurisdictions with different electrical power standards Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
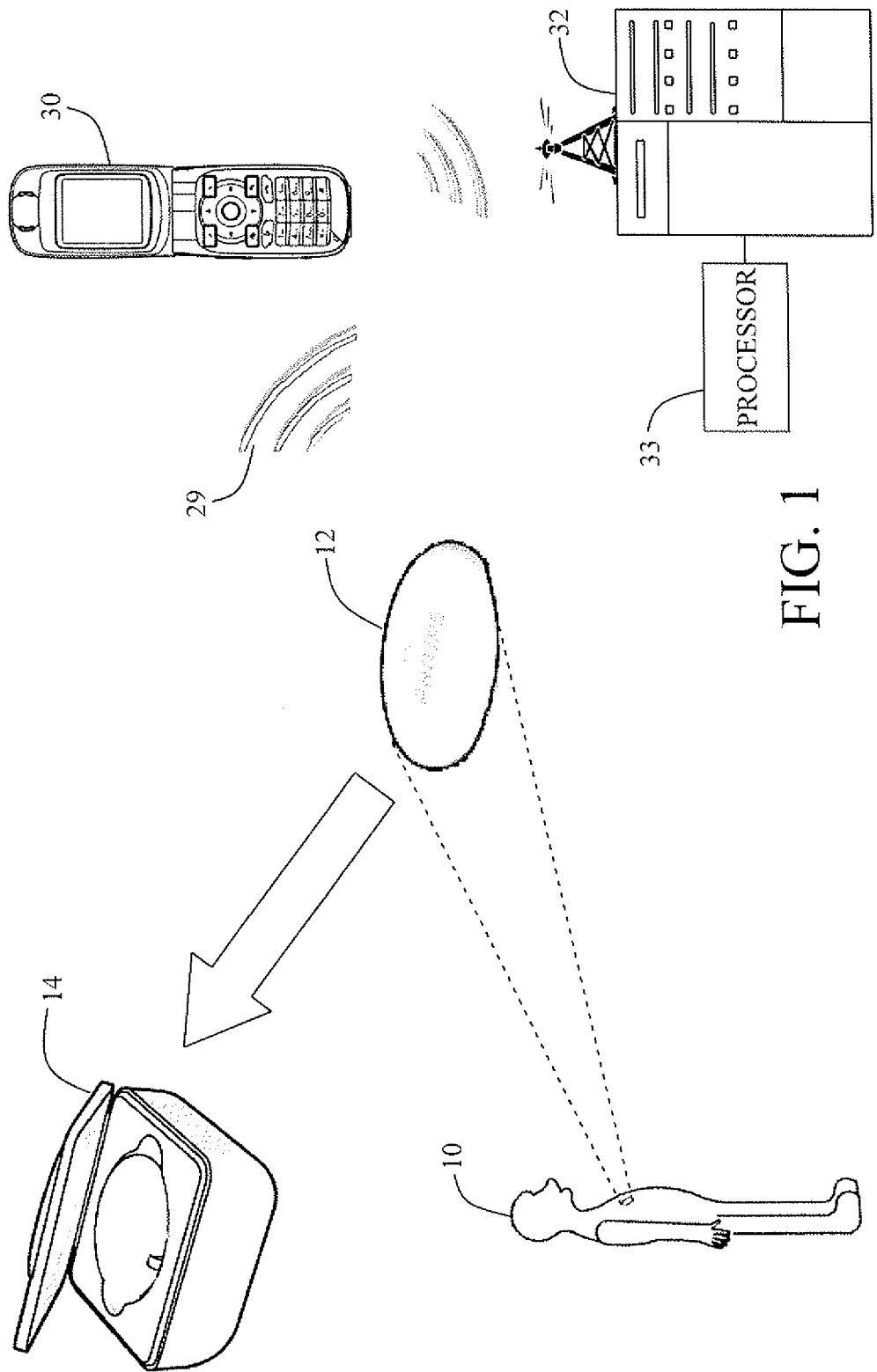
FIG. 1 is an illustration of interaction aspects of a wearable monitor.

With reference to FIG. 1, a patient 10 who either has or is suspected of having a heart or other condition wears a patient monitor 12. The monitor 12 can monitor any physiological condition that is measurable non-invasively. While the monitor 12 in the preferred embodiment measures cardiac activity, a monitor 12 that monitors any of a broad range of conditions are contemplated. In order to detect cardiac signals, the monitor is worn in close proximity to the specific anatomy being monitored. Typically, a doctor prescribes the use of the monitor 12. The patient 10 is supplied with two of the monitors 12, a cordless charger 14, and a supply of skin surface patches. The patient is instructed on preparation of the skin area, applying the patch to the skin area, and how to attach the monitor 12 to the patch so it can start monitoring the physiological process at interest. Typically the patches are replaced every three to seven days. Each time the patient prepares and applies the patch in substantially the same manner. Preferably, the monitor itself 12 is exchanged daily, and the first is charged while the second is monitoring, and vice versa.

Figure 2:
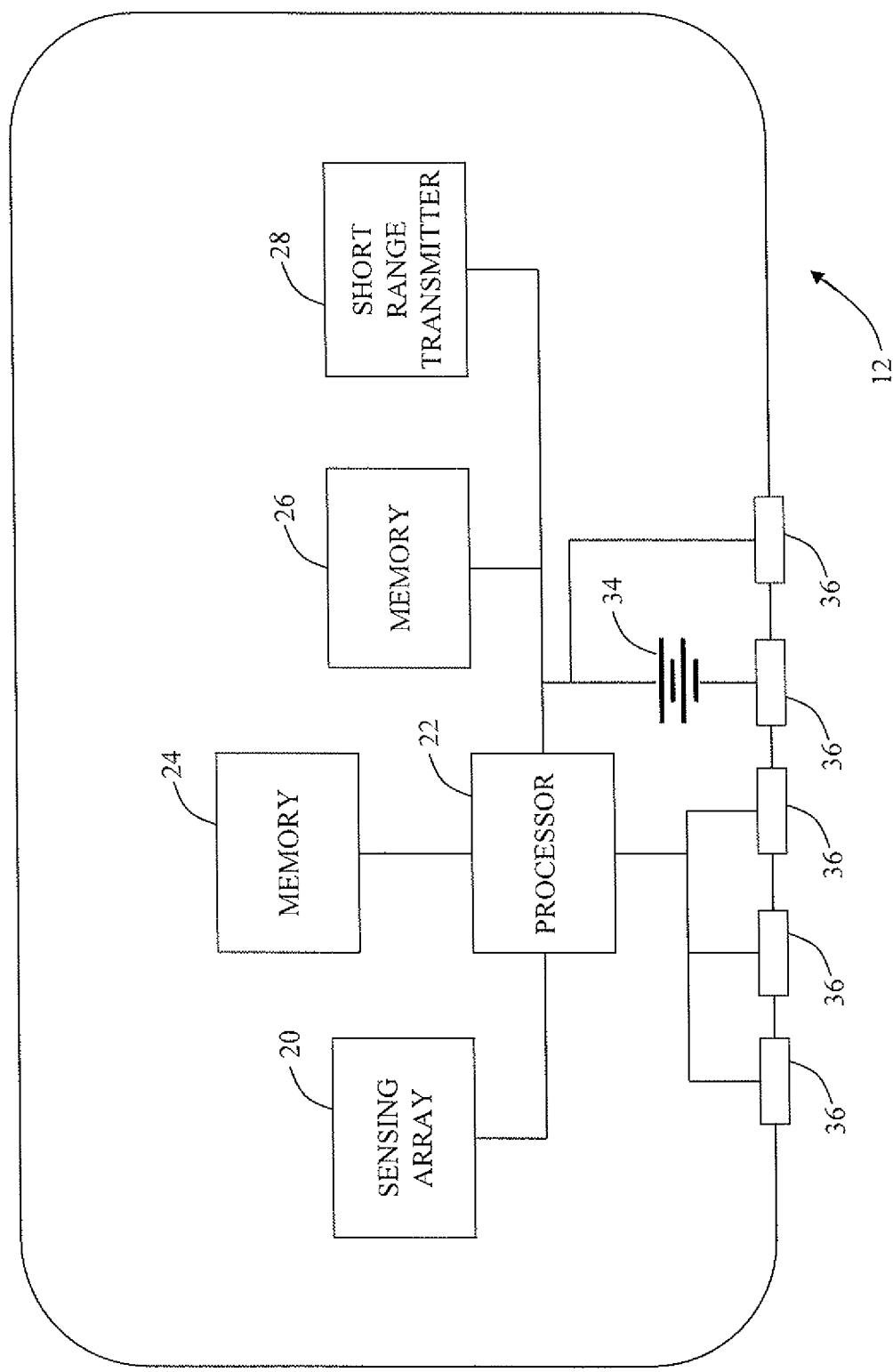
FIG. 2 is a diagrammatic illustration of internal components of an exemplary monitor.

With reference to FIG. 2, the monitor includes a sensing array 20, which senses the physiological process that is to be monitored. The sensing array can include an accelerometer, electrical leads, an acoustic pickup, pressure sensor, or the like The raw data gathered by the sensing array 20 is processed by an on-board processor 22. The processor 22 filters useful information from stray noise, artifacts, background, normal physiological conditions, and other uninteresting information. Since the monitor 12 monitors continuously, vast amounts of information are generated. The processor 22 compares the gathered data to parameters that are pre-programmed into a data parameter or rules memory 24. If, after the comparison is made, the data is determined to be medically significant, it is stored in a collected data memory 26. Otherwise, the data is discarded. Useful data is sent to a data transfer system. Preferably, the data transfer system includes a Bluetooth™ transmitter 28, although other low power transmission protocol are contemplated. With reference again to FIG. 1, the transmitter 28 transmits a short range signal 29 to the patient's Bluetooth enabled cellular telephone 30. It is to be understood that any equivalent to a cellular phone is also contemplated. This includes, but is not limited to PDAs, Pocket PCs, Tablet PCs, laptop computers, RIM BlackBerries, Motorola Q-phones, and other like devices capable of wireless communication. The cell phone 30 then communicates the information collected by the monitor 12 over a cell phone network 31 to a database 32 such as in a computer at the physician's office, hospital, or the like. The database 32 does not have to be resident on a computer, but can be accessible from other devices. Additionally, the information can go to pre-selected third parties as well, such as researchers, statisticians, referring physicians, family members, or the like. Once the data is available, the clinician then can, at any time, review the information collected by the monitors 12 in order to better diagnose and treat the patient 10. In this embodiment, the monitor 12 could transfer the data at a variety of times. For example, the monitor 12 might transmit when the memory 26 is nearly filled to capacity, or it may be set to transmit at regular intervals or at certain times of the day (such as when it is docked in the charger 14).

Another aspect of the monitor's 12 transmission comes in conjunction with emergency situations. If the monitor 12 detects upon comparing detected data with the data or rules in the data parameter memory 24 that a critical situation is present, the monitor 12 triggers the patient's cell phone 30 to contact the appropriate emergency service. Preferably the message would contain the type of situation that the monitor is currently detecting, so the paramedics could be better prepared. Alternately, if detected data differs from normal for the monitored patient, crosses into a pre-selected zone, or is otherwise determined to be significant, the monitored data is sent via the cell phone 30 to the database 32. A processor 33 in conjunction with the database alerts the clinician that data that should be analyzed promptly has been received.

With reference again to FIG. 2, the components 20, 22, 24, 26, and 28 are powered by a battery 34. The monitor battery 34 is preferably a rechargeable lithium-ion cell that has a useful run time that exceeds 24 hours, within a margin of safety. A battery 34 that can operate the monitor 12 for 48 hours or more is preferable. That way, the patient can swap monitors 12 once a day, placing the one that came off the patch into the charger 14 and replacing it with the fully charged monitor 12 that just came out of the charger. For the application described, the battery 34 can be relatively small, e.g., having a capacity of approximately 150 mA hours. This value balances the time needed to perform the task (plus an extra margin of safety) and the size and weight of the battery. Ideally, the battery is as small and as light as possible while still providing adequate power.

The monitor 12 includes contacts 36, which engage matching contacts (not shown) in the charger 14. for receiving a charge when inserted into the charger 14. In the preferred embodiment, the battery 34 in the monitor 12 can receive a full charge (empty to full) promptly, e.g. in approximately three hours. That way, should one of the two monitors fail, the patient will only be without the monitor while it is charging, which will be a relatively short period of time.

Figure 3:
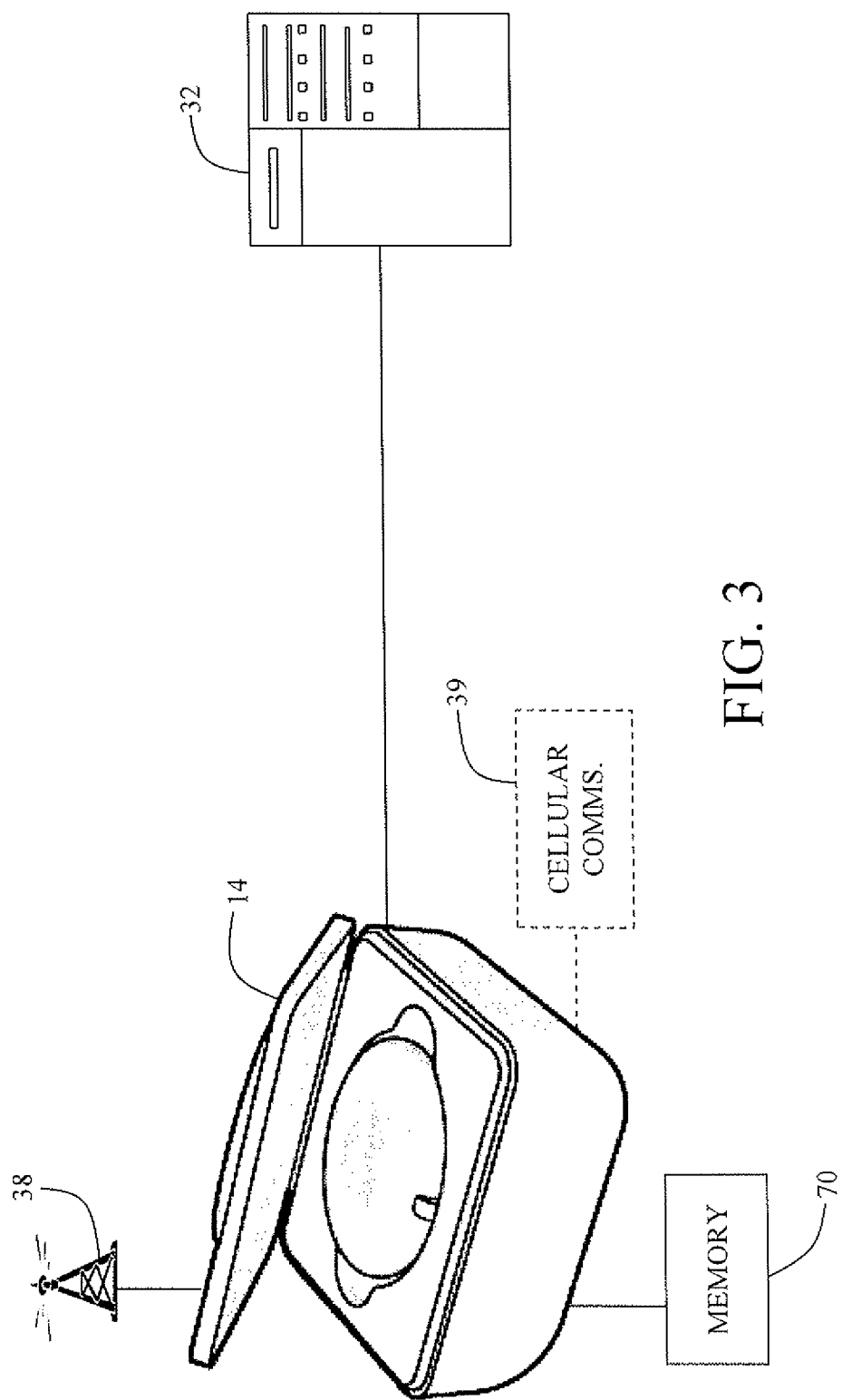
FIG. 3 shows a monitor docked in a cordless charger.

In another embodiment, with reference to FIG. 3, the data transfer system does not include a cellular phone. In this embodiment, cordless charger 14 includes a short range signal receiver 38 and a memory 70. The monitor 12 transmits its data to the charging station where it is stored. Alternately, the data can be downloaded from the monitor to the charging station memory via contacts 36 each time the monitor is charged. The charging station stores the data so it can later be downloaded when the patient turns the monitors 12 and charging station 14 back into the physician. Alternately, the charging station 14 includes a cellular communication circuit 39, and takes the place of the cellular phone 30 of the previous embodiment. In another embodiment, the charger 14 could be adapted to charge the cell phone 30 as well.

In another embodiment, where a patient is supplied with a home monitoring system in addition to the monitors 12, the monitors 12 can transmit data to a temporary storage in the home monitoring system. The home monitoring system then relays the information to off site storage or processing, such as the database 32.

Figure 4:
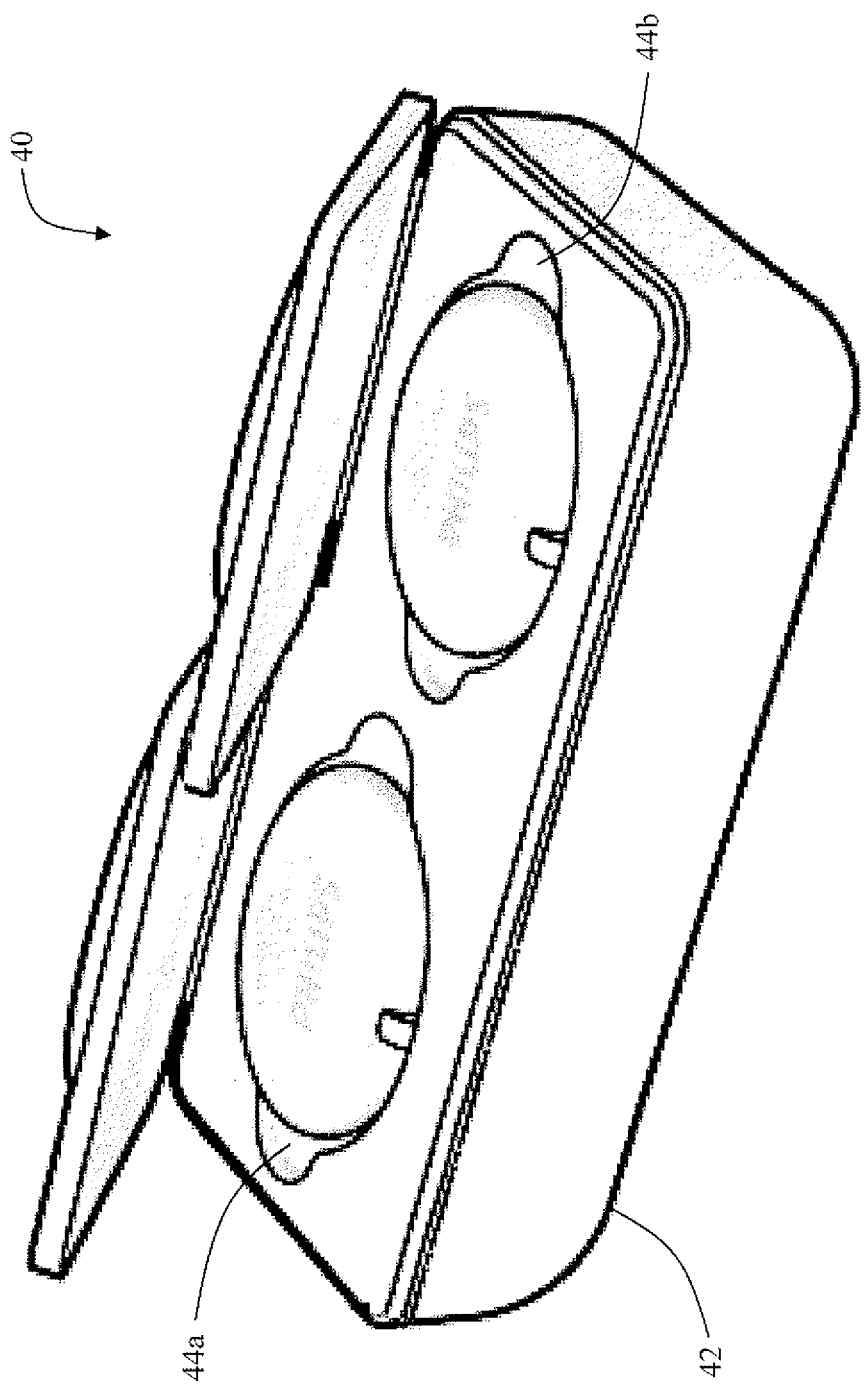
FIG. 4 depicts a cordless charger with two docking bays.

Turning now to FIG. 4, a dual-bay cordless charger 40 is shown. The charger 40 includes a housing 42 with two bays 44a, 44b. The second bay 44b facilitates storage of the second monitor. One or both of the bays 44a, 44b have the appropriate contacts for charging the monitor 12 and receiving information therefrom. An electrically inactive bay may just accommodate the second monitor, when it is not in use. This facilitates keeping paired monitors together between patients. Of course, it is possible that both bays of the charger 40 could be active to charge and transfer information. Additionally, the second bay can also be used for cleaning or sanitizing the monitor 12. For example, the patient can be supplied with a liquid sterilant for the second bay 44b for sanitizing the monitor while not in use. The housing may also include automatic sanitation facilities such as a sterilant or disinfectant injector, heater, timer, or the like.

Figure 5:
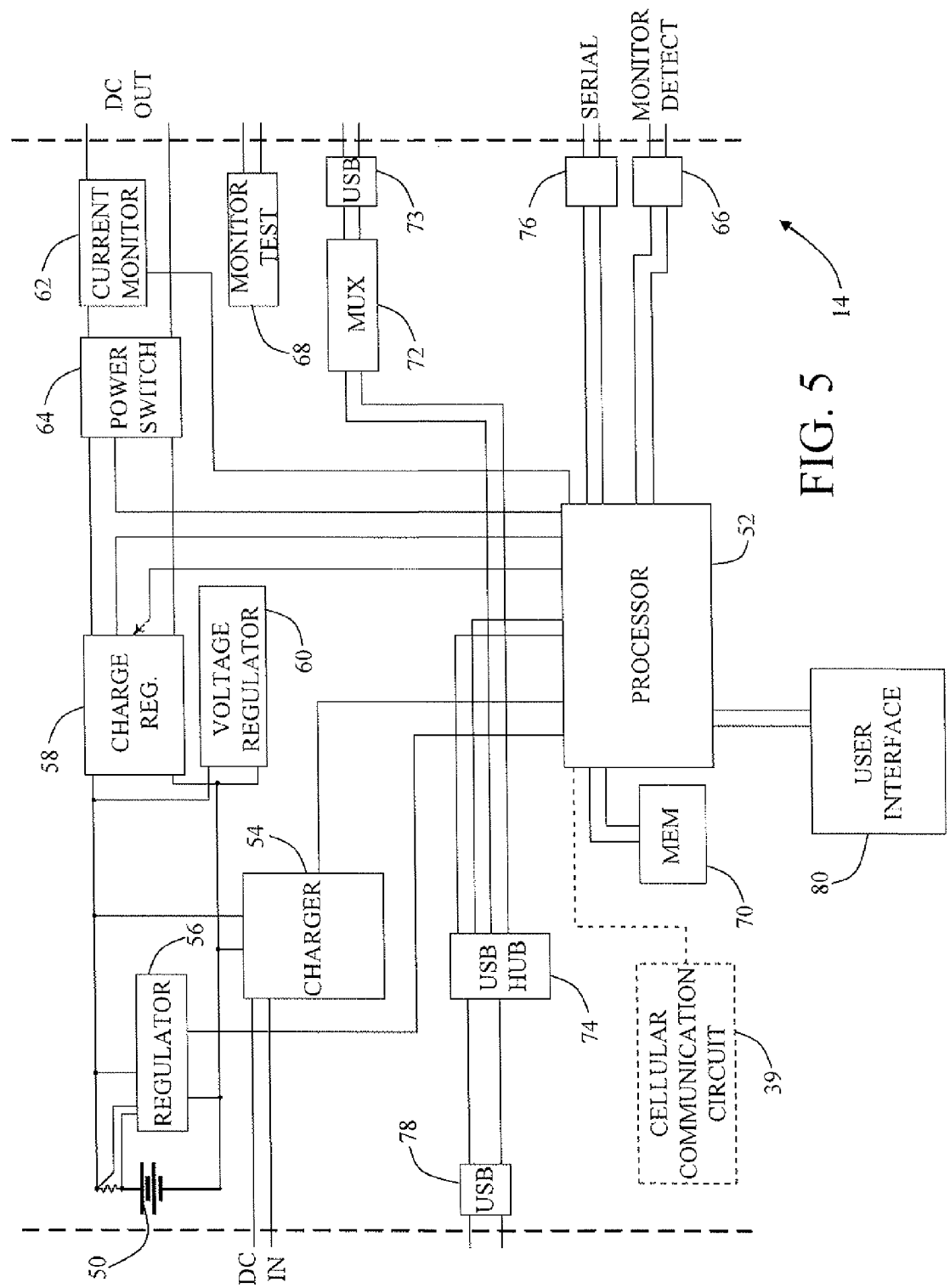
FIG. 5 is a block diagram of the cordless charger.

Now with attention to FIG. 5, a block diagram of the charger 14 is depicted. First and foremost, the charger 14 includes a battery 50 of its own for recharging the batteries 34 of the monitors 12 and for powering its own functions. In one embodiment, the battery 50 is compatible and interchangeable with the patient's cell phone 30, or other wireless device. The charger 14 includes a processor 52 that controls the various sub-processes that occur in the course of the charger's 14 normal operation. The battery 50 itself is rechargeable. In the preferred embodiment, the patient 10 does not have to worry about charging the battery 50 of the charger 14. The battery 50 is charged at a service station and is fully charged when the patient 10 takes possession of it. If a patient is monitored for more than the life of a charge of battery 50, e.g. a month, the charger 14 is replaced on the patient's monthly visit. Preferably, the battery 50 is a lithium ion cell and can be either permanent or removable. If the battery 50 is removable, it could be charged independently of the rest of the charger 14, so that the charger 14 could be field ready with another battery without having to wait for the battery 50 to recharge. Alternately, the battery 50 can be non-rechargeable, removable standard batteries. This would enable (and perhaps require) the patient to replace them. In yet another embodiment, it is contemplated that the charger 14 can be disposable. In the illustrated embodiment, however, a charger 54 receives DC current from an external power supply to charge the battery 50. One or more battery management sub-processors 56 regulates the charging of the battery 50.

A monitor recharging sub-processor 58 oversees the charging of the batteries 34. The battery charge sub-processor 56 works in conjunction with the recharging sub-processor 58 to adjust charging to achieve optimum efficiency. Specifically, the recharging sub-processors balance preserving a life of battery 50 and promptness of charging battery 34. In the preferred embodiment, the battery 50 receives a charge that is sufficient to enable it to charge the batteries 34 of the monitors 12 for about a month, that is, about 30 times. It is also desired to give the battery 50 plenty of extra charges should they be needed, and to account for untraceable losses. The battery 50 is able to charge the monitor batteries 34 about sixty times in the preferred embodiment. In the preferred embodiment, the battery 50 is rated at 4800 mA hours fully charged. Voltage regulators 60 and a current monitor 62 report to the monitor recharging sub-processor 58.

When the battery 50 has 4800 mA hours and the battery 34 has 150 mA hours, the maximum number of full charges is about 4800/150≈32. However, since the battery 34 is typically charged when it is only a third to a half discharged, the number of charges is two to three times this amount. On the other hand, the charging requires a voltage differential between the two batteries. As the battery 50 starts approaching its low voltage limit, the charging rate may be slowed. To optimize the number of recharges and minimize inefficiencies, the voltage difference is reduced when the battery 34 is most drained. As the battery 34 approaches full charge, the charging voltage is increased. When the monitor is fully charged, as sensed by the monitor recharging sub-processor 58, the processor 52 directs a power switch 64 to cut power and stop charging the monitor 12. A monitor detection sensor 66 reports to the processor 52 when the presence of the monitor 12 is detected, so it can determine when to discontinue charging should the monitor 12 be removed prematurely.

The charger 14 also includes a monitor testing sub-processor 68 that runs a diagnostic routine each time a monitor 12 is inserted into the charger 14. This way, the charger 14 detects any malfunctions in the monitors 12. In an embodiment where the charger 14 has no communication capabilities of its own, it a malfunction message is sent to the monitor 12 to report its defect (via Bluetooth through the patient's cell phone 30) to the database 32.

Some embodiments include storage on the charger 14. An SD card or flash memory 70 is connected to the processor 52. These embodiments communicate with the monitor via either USB or serial ports. In a USB embodiment, a signal multiplexor 72 and USB port 73 receive communications from the monitor 12 and rout them to a USB hub 74. The data is processed and stored in the memory 70. In the serial communication embodiment, the processor processes signals from a serial port 76 and stores them in the memory 70. Later, the data can be off-loaded by either removing the SD or flash card 70 or via a USB port 78 which connects with the database 32 either directly or over a remote communication medium such as telephone lines, the internet, a cell phone, or the like.

The charger 14 in some embodiments has a user interface 80. The user interface 80 allows the user to offload data (i.e. over a USB connection) or to program monitors (e.g. setting threshold values, emergency conditions, rules, etc.) over the serial 76 or USB 73 connection.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A patient monitoring system comprising:
    a first wearable patient monitor that is operative to monitor at least one aspect of a patient's physiology, the first monitor including a first rechargeable power source and a first low-power transmitter;
    a second wearable patient monitor that is operative to monitor the at least one aspect of the patient's physiology, the second monitor including a second rechargeable source, and a second low-power transmitter;
    a portable, cordless charger including an internal rechargeable power supply that is operative to recharge the rechargeable power source of the monitor from the internal rechargeable power supply, the portable, cordless charger including a processor that is operative to determine at least one of a battery charging level or a battery charging rate associated with the rechargeable power source of the first and second wearable patient monitors, and a battery level associated with the internal rechargeable power supply of the charger, and wherein the processor is operative to selectively balance a promptness of recharging the rechargeable power source of the first and second wearable patient monitors relative to preserving the battery level determined for the cordless internal rechargeable power supply of the charger by continuously adjusting the charging rate of the rechargeable power source of the first and second wearable patient monitors and a data transfer system that includes a portable wireless communication device external to the first and second wearable patient monitors and the portable cordless charger, the portable wireless communication device including a low-power receiver operative to receive data from the first and second low-power transmitters of the first and second wearable patient monitors, wherein the portable wireless communication device is operative to communicate the data received from the first and second wearable patient monitors to a processor or memory at a remote site.

2. The patient monitoring system as set forth in claim 1, wherein the portable cordless charger includes at least one docking bay in which the first monitor is supported and the first rechargeable power supply is charged while the second monitor is monitoring the at least one aspect of the patient's physiology, and in which the second monitor is supported and the second rechargeable power supply is charged while the first monitor is monitoring the at least one aspect of the patient's physiology.

3. The patient monitoring system as set forth in claim 1, wherein the monitor first transmits data to a temporary storage, which then relays the data to the processor or memory.

4. The patient monitoring system as set forth in claim 1, wherein the monitor rechargeable power supply includes a battery sized to power the monitor for at least 24 hours and wherein the internal power supply of the cordless charger includes a charger battery sized to recharge the monitor battery at least thirty times.

5. The patient monitoring system as set forth in claim 4, wherein the charger battery is removable and replaceable.

6. The patient monitoring system as set forth in claim 1, wherein the monitor further includes:
    a sensor assembly for sensing the physiology aspect; and
    wherein the low power transmitter comprises a short range communications protocol transmitter for transmitting sensed physiological data to the portable wireless communication device, the sensor assembly and the short range transmitter being powered by the rechargeable power supply.

7. The patient monitoring system as set forth in claim 6, wherein the monitor further includes:
    a memory for storing the sensed physiological data and a processor for at least one of (a) determining which sensed physiological data is medically significant and should be transmitted by the short range transmitter and (b) controlling the short range transmitter to transmit the physiological data stored in the memory at intervals, the memory and the processor being powered by the rechargeable power supply.

8. The patient monitoring system as set forth in claim 6, wherein the cordless charger further includes:
a housing having an automatic sanitation facility configured to sanitize the monitor, the automatic sanitation facility comprising at least one of a heater, a sterilant injector, or a disinfectant injector.

9. The patient monitoring system as set forth in claim 1, further including:
a sensor assembly for sensing the physiology aspect;
a memory for storing the sensed physiological data, wherein the physiological data is subsequently transferred to a charger memory and stored.

10. The patient monitoring system as set forth in claim 9, wherein the data from the charger memory is downloaded to a database at a remote site.

11. The patient monitoring system as set forth in claim 9, wherein the data from the charger memory is transmitted from the charger to a database at a remote site.

12. The patient monitoring system as set forth in claim 1, wherein the cordless charger includes at least two docking bays, at least one of the docking bays being functional.

13. A system for patient monitoring comprising:
a first wearable rechargeable patient monitor which monitors at least one aspect of a patient's physiology with a rechargeable power supply source and transfers data from the first monitor to a processor or database at a remote site;
a second wearable rechargeable patient monitor for exchange with the first wearable rechargeable patient monitor to monitor the at least one aspect of the patient's physiology while the first wearable patient monitor is charging, the first wearable rechargeable patient monitor monitoring the at least one aspect of the patient's physiology while the second wearable rechargeable monitor is charging; and,
a cordless charging unit which recharges the first wearable rechargeable patient monitor while the second wearable rechargeable patient monitor is monitoring the at least one aspect of the patient's physiology, wherein the cordless charging unit includes a rechargeable power supply operative to recharge the first wearable rechargeable patient monitor and a processor operative to determine a battery level of the rechargeable power supply, wherein a rate of recharging the power source of the first wearable rechargeable patient monitor is adjusted to preserve a life of the rechargeable power supply of the cordless charging unit.

14. The system as set forth in claim 13, wherein the at least one aspect of the patient's physiology includes cardiac activity.

15. The system as set forth in claim 13, further comprising:
a portable wireless communication device which wirelessly receives the data from either one of the first and second wearable rechargeable patient monitors that is monitoring the at least one aspect of the patient's physiology, and wirelessly retransmits the data by wireless communication to the processor or database at the remote site.

16. The system as set forth in claim 15 wherein the first and second wearable rechargeable patient monitors each have a rechargeable power supply sized to power the monitor for at least 24 hours; and the cordless charging unit has a rechargeable battery sized to charge the power supply at least thirty times.

17. The system as set forth in claim 16, wherein the monitor further includes:
a sensor that senses the at least one aspect of the patient's physiology;
a memory that stores the sensed physiological data;
a processor that processes the sensed physiological data with a processor to determine what portions of the physiological data are useful and what portions are negligible; and
a transmitter that transmits the useful sensed physiological data to the portable wireless communication device;
wherein the rechargeable power supply powers the sensor, the memory, the processor, and the transmitter.

18. The patient monitoring system as set forth in claim 13, wherein the processor of the cordless charging unit is operative to determine at least one of a battery charging level or a battery charging rate associated with the battery of the monitor, and wherein the processor selectively optimizes recharging the battery of the monitor in accordance with the determined battery charging level or battery charging rate relative to the battery level determined for the cordless charging unit.

19. A patient monitoring system comprising:
at least one wearable rechargeable monitor which includes a sensor for sensing physiological data from a patient wearing the monitor, a low power transmitter which transmits the physiological data, and a rechargeable power source which powers the sensor and the low power transmitter;
a data transfer device which receives the physiological data from the low power transmitter and re-transmits the physiological data to a processor or a memory at a remote site;
a cordless recharging station remote from the patient which recharges the at least one wearable rechargeable monitor when it is not worn by the patient, the cordless recharging station including a rechargeable power supply operative to recharge the at least one wearable rechargeable monitor and a processor operative to determine a battery level of the rechargeable power supply, wherein recharging of the monitor is optimized by balancing a promptness of recharging the power source of the monitor relative to preserving a life of the cordless recharging station.

20. The system as set forth in claim 19, wherein the at least one wearable rechargeable monitor includes at least two wearable rechargeable monitors such that one of the at least two wearable rechargeable monitors is charged while another of the at least two monitors is worn and senses the physiological data.

21. The system as set forth in claim 20, wherein the processor of the cordless recharging station is operative to determine at least one of a battery charging level or a battery charging rate associated with the battery of the monitor, and wherein the processor is operative to selectively optimize recharging the battery of the monitor in accordance with the determined battery charging level or battery charging rate relative to the battery level determined for the cordless recharging station.

* * * * *